United States Patent
Kakimoto et al.

(10) Patent No.: US 6,417,411 B2
(45) Date of Patent: Jul. 9, 2002

(54) METHOD FOR PRODUCTION OF ETHYLENE GLYCOL

(75) Inventors: Yukihiko Kakimoto, Yokohama; Yoshihisa Oka, Chigasaki, both of (JP)

(73) Assignee: Nippon Shokubai Co., Ltd., Osaka (JP)

( * ) Notice: Subject to any disclaimer, the term of this patent is extended or adjusted under 35 U.S.C. 154(b) by 0 days.

(21) Appl. No.: 09/844,478

(22) Filed: Apr. 27, 2001

(30) Foreign Application Priority Data

May 8, 2000 (JP) ........................................ 2000-134796

(51) Int. Cl.$^7$ ............................................... C07C 29/10

(52) U.S. Cl. ...................... 568/867; 549/534

(58) Field of Search ......................... 568/867; 549/534

(56) References Cited

PUBLICATIONS

Ozawa, "From Basis to Technological Development", Chemical Process, 1$^{st}$ Edition 1$^{st}$ Impression Published on Mar. 25, 1998.

*Primary Examiner*—Ba K. Trinh
(74) *Attorney, Agent, or Firm*—Fish & Richardson P.C.

(57) ABSTRACT

In a composite process for subjecting ethylene to catalytic gas phase oxidation thereby obtaining ethylene oxide and causing this ethylene oxide to react with water thereby obtaining ethylene glycol, a method for producing the ethylene glycol is provided which permits effective utilization of the energy at the step for dehydrating and concentrating the resultant aqueous ethylene glycol solution. In the production of ethylene glycol by the supply of the aqueous ethylene glycol solution to a concentrating treatment at the multi-effect evaporator, the method contemplated by this invention for the production of ethylene glycol comprises utilizing as the source of heating at least one specific step the steam generated in the multi-effect evaporator.

10 Claims, 1 Drawing Sheet

METHOD FOR PRODUCTION OF ETHYLENE GLYCOL

BACKGROUND OF THE INVENTION

1. Field of the Invention

This invention relates to a method for the production of ethylene glycol. Particularly this invention pertains, in a composite process for obtaining ethylene oxide by catalytic gas phase oxidation of ethylene and causing the ethylene oxide to react with water thereby obtaining ethylene glycol, to a method for the production of ethylene glycol by advantageously utilizing in the composite process mentioned above the vapor generated in the multi-effect evaporator used in the step for concentrating the produced aqueous ethylene glycol solution.

2. Description of the Related Art

Ethylene glycol is usually produced by the reaction of ethylene oxide with water. Then, the ethylene oxide is produced nowaday by the catalytic gas phase oxidation of ethylene with a molecular oxygen-containing gas in the presence of a silver catalyst. The process for the production of ethylene oxide is roughly as follows.

The reaction gas containing ethylene oxide formed by the catalytic gas phase oxidation of ethylene with molecular oxygen-containing gas on the silver catalyst is introduced to an ethylene oxide absorber and brought into contact with an absorption liquid having water as a main component to recover the aqueous ethylene oxide solution and then forwarded to an ethylene oxide stripper so as to cause stripping of the ethylene oxide from the aqueous solution by heating the bottom portion of the ethylene oxide stripper with steam, the aqueous solution containing substantially no ethylene oxide and obtained from the bottom portion of the ethylene oxide stripper is cyclically used as the absorption liquid, The stripped products such as the ethylene oxide obtained from the top of the ethylene oxide stripper, water, carbon dioxide, inert gas (such as nitrogen, argon, methane, and ethane), such low boiling impurities as formaldehyde, and high boiling impurities as acetaldehyde and acetic acid are forwarded through the dehydration step, the light end separation step, and the heavy end separation step to obtain purified ethylene oxide. Portion of the gas containing the unreacted ethylene, by-produced carbon dioxide, and inert gases (such as nitrogen, argon, methane, and ethane) may be circulated to the ethylene oxidation step. Normally, it is partially separated and introduced to the carbon dioxide absorber so that carbon dioxide may be selectively absorbed therein and the absorbed solution may be treated to recover carbon dioxide therefrom by stripping.

The aqueous solution containing monoethylene glycol, diethylene glycol, triethylene glycol, tetraethylene glycol, and polyethylene glyol which are obtained by the reaction of purified or crude ethylene oxide consequently formed with water is deprived of the water by vaporization as in a multi-effect evaporator. The concentration consequently obtained is dehydrated to a high degree and further purified sequentially in a monoethylene glycol distillation column, a diethylene glycol distillation column, and a triethylene glycol distillation column to obtain purified ethylene glycols. Incidentally, in the ethylene oxide absorber even in the process for the production of ethylene oxide, the reaction occurs between water with ethylene oxide and forms ethylene glycol.

The absorbing solution is partly separated and similarly concentrated in the multi-effect evaporator and/or the dehydration distillation column to obtain the various ethylene glycol products(Refer, for example, to "Chemical Process—Fundamentals to Development of Technique—" compiled by Society of Chemical Engineering and published by Tokyo Kagaku Dojin on Mar. 25, 1998, pages 121–128.).

The production of ethylene glycol from ethylene via ethylene oxide as described above entails various operations such carbon dioxide stripping operation, ethylene oxide stripping operation, dehydrating operation, light end separating operation, an ethylene oxide rectifying operation, by-produced ethylene glycol concentrating and dehydrating operation, and further mono-, di-, and triethylene glycol rectificating operations. Since these operations consume large amount of heat, they are under obligation to control supply of the heat volumes efficiently.

An object of this invention, therefore, is to provide for a composite process which subjects ethylene to catalytic gas-phase oxidization and causes the resultant ethylene oxide to react with water to produce ethylene glycol a method for the production of ethylene glycol which comprises advantageously utilizing for the composite process the steam generated at a multi-effect evaporator used at the step for dehydrating the aqueous ethylene glycol solution obtained by the composite process.

SUMMARY OF THE INVENTION

We, after pursuing a diligent study in search of a solution for the problems mentioned above, have conceived an idea of advantageously utitilizing the energy of the steam generated from a multi-effect evaporator serving to evaporate and concentrate the aqueous ethylene glycol solution obtained by the reaction of ethylene oxide with water. We have found that the problems mentioned above are consequently solved. This invention has been perfected as a result.

The object of this invention mentioned above is accomplished by the following item (1) and (2).

(1) A method for the production of ethylene glycol which in producing by the catalytic gas phase oxidation of ethylene with a molecular oxygen-containing gas in the presence of a silver catalyst to obtain ethylene oxide and causing the resultant ethylene oxide to react with water thereby producing an aqueous ethylene glycol solution and subjecting this aqueous solution to a concentrating operation with a multi-effect evaporator and dehydrating this aqueous solution and producing ethylene glycol, which comprises using the vapor generated in the multi-effect evaporator mentioned above as the source for heating at least one of the following steps (A)–(H):

(A) a step of introducing an ethylene oxide-containing gas formed by the reaction of catalytic gas phase oxidation to an ethylene oxide absorber, causing the gas to contact an aqueous medium absorption solution and form ethylene oxide-containing bottoms therein, introducing the bottom to an ethylene oxide stripper, and separating ethylene oxide by heating the bottoms of the stripper, (B) a step of circulating portion of the gas from the top of the ethylene oxide absorber to the ethylene oxidation step and introducing the remainder thereof to a carbon dioxide absorber and allowing it to contact with an alkali absorption solution to obtain a carbon dioxide-containing bottom, and introducing the bottoms to the carbon dioxide stripper, and heating the bottoms of the stripper thereby separating carbon dioxide, (C) a step of introducing an aqueous ethylene oxide solution obtained by concentrating the gas from the top of the ethylene oxide stripper to the ethylene oxide dehydration column and heating the bottoms of the dehydration column thereby separating light end components such as ethylene oxide, (D) a step of introducing the ethylene oxide-containing fraction obtained by condensing the gas from the top of the dehydration column to the light end separation column, heating the bottoms of this separation column thereby separating the light weight component, and obtaining crude ethylene oxide as the bottoms, (E) a step of introducing the crude ethylene oxide to the ethylene oxide rectifying column and heating the bottoms of the rectifying column thereby obtaining purified ethylene oxide from the top of the rectifying column, (F) a step of extracting portion of the absorption solution obtained through the bottom of the ethylene oxide stripper, introducing it to the by-produced ethylene glycol concentration column and heating the bottoms of the concentration column thereby effecting dehydration and concentration, (G) a step of introducing an aqueous ethylene glycol solution obtained at the multi-effect evaporator and concentrated therein to the ethylene glycol dehydration column, heating the bottoms of the dehydration column thereby effecting substantial separation of the water through the top of the column, and (H) a step of introducing the solution of the ethylene glycol dehydration column substantially deprived of water to the monoethylene glycol distillation column bottoms, heating the bottoms of the distillation column thereby separating and obtaining monoethylene glycol from the top of the column.

(2) A method according to claim (1), wherein the number of multi-effect evaporators to be used is at least three and the steam to be utilized as the heating source has pressure in the range of −0.08 to 1.2 MPa (Gauge).

It has been demonstrated that by partly removing the steam generated in the top portion of the multi-effect evaporator and utilizing the removed steam as the source for heating the other steps, it is made possible to recover the thermal energy possessed by the steam, attain effective utilization of energy and, with a smaller consumption of the energy than the total amount of energy used at the other steps and in the other multi-effect evaporator, fulfill the distillation at the other steps and the evaporation and concentration in the multi-effect evaporator.

EXPLANATION OF THE PREFERRED EMBODIMENTS

Figure 1:
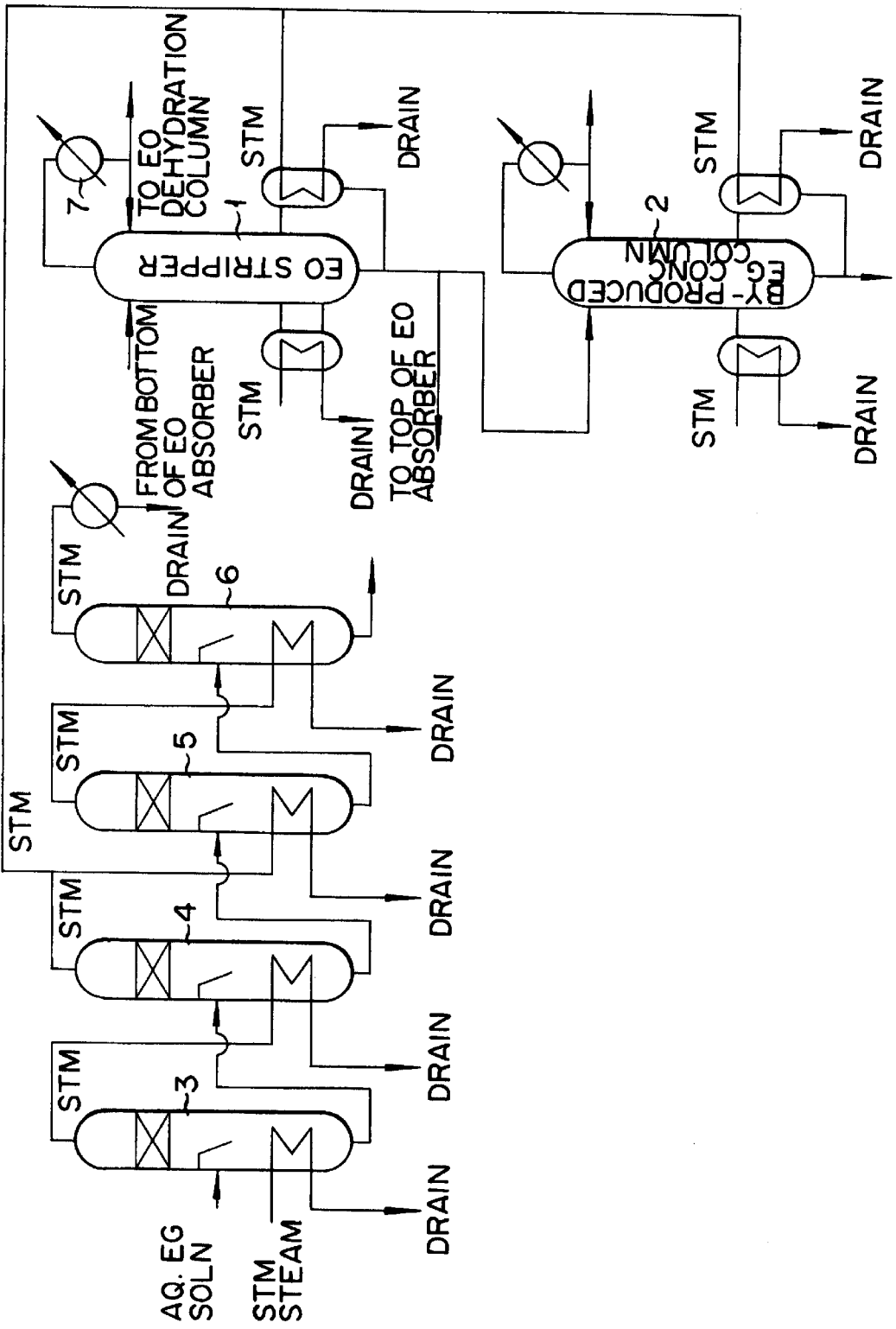
FIG. 1 is a process flow sheet illustrating the typical process in working Example 1 and Control 1.

Now, this invention will be specifically explained below with reference to preferred mode of embodying this invention below.

The reaction of ethylene oxide with water is carried out under the following conditions. A molar ratio of ethylene oxide and water, namely ethylene oxide:water, is in the range of 1:7–1:50, preferably 1:5–1:30. A reaction pressure is in the range of 0.5–3.0 MPa (Gauge), preferably 1.5–2.5 MPa (Gauge), a reaction temperature is in the range of 120°–250° C., preferably 130°–180° C., and a concentration of the formed ethylene glycol was in the range of 5 –40 mass %. The reaction is carried out in the batch-wise, the semibatch-wise, or the continuously, which ever fits the occasion best. The ethylene glycol thus obtained is supplied to the multi-effect evaporator and concentrated and dehydrated till a concentration of 40–95 mass % or over.

The number of multi-effect evaporators is described in detail at pages 428–431 of the Handbook on Chemical Engineering (fourth revised edition, published by Maruzen Publishing Co., Ltd. on Jan. 20, 1984). The number of multi-effect evaporators ought to be not less than two and is decided in consideration of the cost of equipment and the cost of energy to be involved. In this invention, it is in the range of 3–5. When a first evaporator is supplied with the initial energy, the interiors of a second and subsequent evaporators are sequentially concentrated with steam which enters through the top of the preceding evaporator having a higher operation pressure. This invention does not need to discriminate particularly the heat source for initial energy on account of the kind of initial energy. Preferably, steam or such molten salt as Dowtherm (a heat transfer medium made and sold by the Dow Chemical Co.) or niter is used as the heat medium. The pressure in the first evaporator to which the initial energy is supplied does not need to be particularly limited. It is decided in due consideration of the fact that the pressure be effectively utilized for heating the evaporators to be operated at the subsequent steps. Generally, the pressure is in the range of 0.20–2.5 MPa (Gauge), preferably in the range of 0.5–1.2 MPa (Gauge).

The mode of the multi-effect evaporator is known in three types, i.e. normal flow, reverse flow, and complex flow. This invention permits use of any of these types. Further, the evaporator is in such a style that it may be furnished with a tray or a packing intended to decrease the amount of a heavy-weight component which is liable to entrain the steam in flow.

In this invention, the second and subsequent evaporators are operated under sequentially lowered working pressures. The pressure of the steam obtained therefrom is in the range of −0.08 to 1.2 MPa (Gauge), preferably in the range of −0.05 to 0.5 MPa (Gauge). The steam of this pressure is utilized advantageously in this invention. The drainage which is generated from each of the evaporators has only a small amount of heat and is reclaimed rather as a raw material for the generation of steam than as a heat source.

The amount of heat of the steam which is consequently obtained as described is effectively utilized at such steps of producing ethylene oxide and ethylene glycol as described below. Now, the operating conditions for the component steps defined by this invention will be specifically described below.

A: Conditions for ethylene oxide stripper:

The pressure at the top of the column is in the range of 0.01–0.2 MPa (Gauge), preferably in the range of 0.03–0.06 MPa (Gauge).

The temperature of the top of the column is in the range of 85°–120° C., preferably in the range of 90°–100° C., and the temperature at the bottom of the column is in the range of 100°–150° C., preferably in the range of 110°–120° C.

B: Conditions for carbon dioxide stripper:

The operation pressure of this column is in the range of 0–0.05 MPa (Gauge), preferably in the range of 0.001–0.02 MPa (Gauge), and the temperature at the bottom of the column is in the range of 80°–120 20 C., preferably in the range of 100°–110° C.

C: Conditions for ethylene oxide dehydration column:

The pressure at the top of the column is in the range of 0–0.5 MPa (Gauge), preferably in the range of 0.01–0.05 MPa (Gauge).

The temperature at the top of this column is in the range of 10°–60° C., preferably in the range of 15°–20° C., and the temperature at the bottom of this column in the range of 10°–130° C., preferably in the range of 20°–40° C.

D: Conditions for light end separation column:

The pressure at the top of this column is in the range of 0.1–1 MPa (Gauge), preferably in the range of 0.3–0.7 MPa (Gauge).

The temperature at the top of the column is in the range of 30°–90° C., preferably in the range of 45°–80° C., and the temperature at the bottom of the column is in the range of 30°–90° C., preferably in the range of 45°–80° C.

E: Conditions for ethylene oxide rectification column:

The pressure at the top of this column is in the range of 0.1–0.8 MPa (Gauge), preferably in the range of 0.2–0.5 MPa (Gauge).

The temperature at the top of the column is in the range of 30°–80° C., preferably in the range of 40°–65° C., and the temperature at the bottom of the column is in the range of 35°–85° C., preferably in the range of 45°–70° C.

F: Conditions for by-produced glycol concentration column:

The pressure at the top of this column is in the range of 0.08–0.2 MPa (Gauge), preferably in the range of 0–015 MPa (Gauge).

The temperature at the top of the column is in the range of 60°–150° C., preferably in the range of 70°–110° C., and the temperature at the bottom of the column is in the range of 70°–200° C., preferably in the range of 80°–120° C.

The concentration of ethylene glycol at the bottom of this column is in the range of 10–90 mass %, preferably in the range of 70–90 mass %.

G: Conditions for ethylene glycol dehydration column:

The pressure in this column is in the range of 50–500 hPa, preferably in the range of 90–140 hPa.

The temperature at the top of the column is in the range of 30°–80° C., preferably in the range of 45°–55° C. and the temperature at the bottom of the column in the range of 80°–120° C., preferably in the range of 90°–110° C.

H: Conditions for monoethylene glycol distillation column:

The pressure in the column is in the range of 10–70 hPa, preferably in the range of 25–55 hPa.

The temperature at the top of the column is in the range of 85°–125° C., preferably in the range of 100°–120° C. and the temperature at the bottom of this column in the range of 90°–130° C, preferably in the range of 105°–125° C.

Thus, ethylene glycol is produced from ethylene oxide as the starting raw material. This ethylene glycol, besides the monoethylene glycol mentioned above, sequentially forms diethylene glycol, triethylene glycol, tetraethylene glycol, and polyethylene glycol by causing the bottom of the distillation column to be subjected to the subsequent distillation conditions.

The stripper, dehydration column, separation column, rectification column, and concentration column which are defined by this invention are invariably in the type of an ordinary distillation column and may be furnished with a tray or a packing. As typical examples of the tray suitably used herein, a bubble cap tray, a sieve tray, and a ballast tray may be cited. As typical examples of the packing, Raschig ring, ball rings, saddle rings, McMahon packing, Interlocks Metal Packing (made by Norton Co. of U.S.), Merapack (made by Sulzer of Switzerland), and Sulzer BX Packing (made by Sulzer of Switzerland) may be cited.

To demonstrate the effect of this invention, the following working examples and controls will described below.

Example 1 (Refer to FIG. 1)

A gaseous ethylene oxide-containing reaction product obtained by the catalytic gas phase oxidation of ethylene with a molecular oxygen-containing gas in the presence of a silver catalyst was supplied to the lower part of an ethylene oxide absorber and an absorption solution (water) was introduced from the upper portion of the absorber and brought into counterflow contact with the gas reaction product till the ethylene oxide in the gaseous reaction product was absorbed in the absorption solution (water). The gas escaping the absorption and emanating from the top of the absorber was circulated to an ethylene oxide reactor. As illustrated in FIG. 1, the bottom liquid in the absorber was supplied to the upper portion of an ethylene oxide stripper 1 having the pressure at the top thereof fixed at 0.045 MPa (Gauge) and the temperature at the bottom thereof fixed at 115° C., portion of the bottom liquid forwarded to a by-produced ethylene glycol concentration column 2 having the pressure at the top thereof fixed at 0.076 MPa (Gauge) and the temperature at the bottom thereof fixed at 122° C., the remainder thereof circulated to the ethylene oxide absorber (not illustrated), and the ethylene oxide-containing stripping steam emanating from the top of the ethylene oxide stripper 1 was condensed in a condenser 7, portion of the condensed vapor was refluxed to the ethylene oxide stripper 1 and another portion was supplied to an ethylene oxide dehydration column (not illustrated). The ethylene oxide-containing vapor emanating from the top of the dehydration column was condensed in a condenser (not illustrated) and portion thereof was refluxed to the dehydration column and the reminder thereof was supplied to the light-end separation column (not illustrated). The uncondensed steam in the condenser was supplied to the ethylene oxide reabsorption column (not illustrated). The steam emanating from the top of the light end separation column was forwarded to the condenser, the condensate consequently formed was refluxed to the light end separation column, and the uncondensed steam in the condenser was supplied to the ethylene oxide reabsorption column. The bottom liquid in the light end separation column was forwarded to the ethylene oxide rectification column. The ethylene oxide vapor emanating from the top of the column was condensed in the condenser and portion of the condensed vapor was refluxed to the ethylene oxide rectification column (not illustrated) and the other portion thereof was extracted as a product of ethylene oxide. The bottom liquid in the ethylene oxide rectification column was separated for the purpose of separating such high-boiling substances as aldehyde and acetic acid.

Meanwhile, the aqueous solution containing ethylene oxide was separated from the bottom portion of the ethylene oxide dehydration column (not illustrated) and was forwarded together with ethylene oxide as a product to the hydration device, left reacting therein at a pressure of 1.8 MPa (Gauge) and a reaction temperature of 150° C. The aqueous ethylene glycol solution consequently obtained in an amount of 15.2 mass % was forwarded to a first evaporator 3 operated with the pressure at the top thereof fixed at 0.41 MPa (Gauge) and the temperature of the interior liquid at 153° C.

The bottom liquid in the first evaporator 3 was forwarded to a second evaporator 4 operated with the pressure at the top of the column fixed at 0.17 MPa and the temperature in the bottom part thereof at 136° C., the steam emanating from the top part of the first evaporator 3 was used as the heat source for the heating device, the bottom liquid in the second evaporator 4 was forwarded to the third evaporator 5 operated with the pressure in the top of the column fixed at 0.07 MPa (Gauge) and the temperature in the bottom thereof at 124° C., the steam in the top of the second evaporator 4 was partly used as the heat source for the heating device of the third evaporator 5, the remainder thereof was used as the heat source for the heating device for heating the by-produced ethylene glycol concentration column, and the bottom liquid in the third evaporator 5 was forwarded to a fourth evaporator 6 operating with the pressure in the top thereof fixed at 0.03 MPa (Gauge) and the temperature in the bottom thereof fixed at 105° C., the steam in the top portion of the third evaporator 5 was used as the heat source for the heating device of the fourth evaporator 6, the bottom liquid in the fourth evaporator 6 was forwarded to the ethylene glycol dehydration column and deprived of the water entrained thereby and then forwarded to the monoethylene glycol distillation column (not illustrated) till monoethylene glycol was separated through the top thereof. The bottom liquid in the monoethylene glycol distillation column was forwarded to the diethylene glycol distillation column (not illustrated) to separate diethylene glycol through the top of the column. The bottom liquid in the column was forwarded to the triethylene glycol distillation column (not illustrated) to separate triethylene glycol through the top of the column.

The procedure described above was repeated for each of the component steps illustrated in the diagram. The operating conditions used therefor, the performance of the steam produced, and the amount thereof consumed are shown in Table 1.

Control 1

In the procedure of Example 1, the multi-effect evaporators, the ethylene oxide stripper, and the by-produced ethylene glycol concentration column were operated on the condition that all the steam from the top of the second evaporator 4 would be wholly used as the heat source for the heating device of the third evaporator 5. The operating conditions used herein, the performance of the steam produced, and the amount thereon consumed are shown in Table 1.

TABLE 1

|  |  | Example 1 | Control 1 |
|---|---|---|---|
| Amount of steam used |  |  |  |
| Multi-effect evaporator | ton/hr | 28.8 | 18.1 |
| Ethylene oxide stripper (1) | ton/hr | 9 | 26 |
| By-produced ethylene glycol concentration column | ton/hr | 4 | 12 |
| Total | ton/hr | 41.8 | 56.1 |
| Operating conditions for multi-effect evaporator |  |  |  |
| First evaporator (3) |  |  |  |
| Pressure at the top | MPa | 0.41 | 0.57 |
| Temperature at the top | ° C. | 153 | 163 |
| Temperature in the bottom portion | ° C. | 159 | 166 |
| Amount of steam at the top | ton/hr | 26.7 | 17.8 |
| Amount of liquid at inlet | ton/hr | 93.3 | 93.3 |
| Glycol concentration at inlet |  | 15.2 | 15.2 |
| Glycol concentration in bottom portion of the column |  | 20.8 | 18.8 |
| Second evaporator (4) |  |  |  |
| Pressure at the top | MPa | 0.17 | 0.36 |
| Temperature at the top | ° C. | 130 | 149 |
| Temperature in the bottom | ° C. | 136 | 152 |
| Amount of steam at the top | ton/hr | 7 | 18.6 |
| Amount of steam separated to the other steps | ton/hr | 25 | 0 |
| Glycol concentration in bottom liquid in the column |  | 39 | 24.9 |
| Third evaporator (5) |  |  |  |

TABLE 1-continued

|  |  | Example 1 | Control 1 |
|---|---|---|---|
| Pressure at the top | MPa | 0.17 | 0.16 |
| Temperature in the top portion | ° C. | 115 | 129 |
| Temperature in the bottom portion | ° C. | 124 | 135 |
| Amount of steam at the top | ton/hr | 7.7 | 19.2 |
| Glycol concentration in bottom liquid of the column |  | 50.2 | 37.6 |
| Fourth evaporator (6) |  |  |  |
| Pressure in the top portion | MPa | −0.03 | −0.03 |
| Temperature in the top portion | ° C. | 90 | 90 |
| Temperature in the bottom portion | ° C. | 105 | 105 |
| Amount of steam through the top | ton/hr | 7.2 | 18 |
| Glycol concentration in bottom liquid of the column |  | 72 | 72 |

The entire disclosure of Japanese Patent Application No. 2000-134796 filed on May 8, 2000 including specification, claims, drawings and summary are incorporated herein by reference in its entirety.

What is claimed is:

1. A method for the production of ethylene glycol which in producing by the catalytic gas phase oxidation of ethylene with a molecular oxygen containing gas in the presence of a silver catalyst to obtain ethylene oxide and causing the resultant ethylene oxide to react with water thereby producing an aqueous ethylene glycol solution and subjecting this aqueous solution to concentrating operation with a multi-effect evaporator and dehydrating this aqueous solution and producing ethylene glycol, which comprises using the vapor generated in the multi-effect evaporator mentioned above as the source for heating at least one of the following steps (A)–(H):

(A) a step of introducing an ethylene oxide-containing gas formed by the reaction of catalytic gas phase oxidation to an ethylene oxide absorber, causing the gas to contact an aqueous medium absorption solution and form ethylene oxide-containing bottoms therein, introducing the bottom to an ethylene oxide stripper, and separating ethylene oxide by heating the bottoms of the stripper, (B) a step of circulating portion of the gas from the top of the ethylene oxide absorption column to the ethyelene oxidation step and introducing the remainder thereof to the carbon dioxide absorption column and allowing it to contact with an alkali absorption solution to obtain the carbon dioxide-containing bottom, and introducing the bottoms to the carbon dioxide stripper, and heating the bottoms of the stripper thereby separating carbon dioxide, (C) a step of introducing an aqueous ethylene oxide solution obtained by concentrating the gas from the top of the ethylene oxide stripper to the ethylene oxide dehydration column and heating the bottoms of the dehydration column thereby separating light end components such as ethylene oxide, (D) a step of introducing the ethylene oxide-containing fraction obtained by condensing the gas from the top of the dehydration column to the light end separation column, heating the bottoms of this separation column thereby separating the light end component, and obtaining crude ethylene oxide as the bottoms, (E) a step of introducing the crude ethylene oxide to the ethylene oxide rectifying column and heating the bottoms of the rectifying column thereby obtaining purified ethylene oxide from the top of the rectifying column.

(F) a step of extracting portion of the absorption solution obtained through the bottom of the ethylene oxide stripper, introducing it to the by-produced ethylene glycol concentration column and heating the bottoms of the concentrating column thereby effecting dehydration and concentration.

(G) a step of introducing the aqueous ethylene glycol solution obtained at the multi-effect evaporator and concentrated therein to the ethylene glycol dehydration column, heating the bottoms of the dehydration column thereby effecting substantial separation of the water through the top of the column.

(H) a step of introducing the solution of the ethylene glycol dehydration column substantially deprived of water to the monoethylene glycol distillation column bottoms, heating the bottoms of the distillation column thereby separating and obtaining monoethylene glycol from the top of the column.

2. A method according to claim 1, wherein the number of multi-effect evaporators to be used is at least three and the steam to be utilized as the heating source has pressure in the range of −0.08–1.2 MPa (Gauge).

3. A method according to claim 1, wherein the vapor generated in the multi-effect evaporator is used as the source for heating of the step (A).

4. A method according to claim 1, wherein the vapor generated in the multi-effect evaporator is used as the source for heating of the step (B).

5. A method according to claim 1, wherein the vapor generated in the multi-effect evaporator is used as the source for heating of the step (C).

6. A method according to claim 1, wherein the vapor generated in the multi-effect evaporator is used as the source for heating of the step (D).

7. A method according to claim 1, wherein the vapor generated in the multi-effect evaporator is used as the source for heating of the step (E).

8. A method according to claim 1, wherein the vapor generated in the multi-effect evaporator is used as the source for heating of the step (F).

9. A method according to claim 1, wherein the vapor generated in the multi-effect evaporator is used as the source for heating of the step (G).

10. A method according to claim 1, wherein the vapor generated in the multi-effect evaporator is used as the source for heating of the step (H).

* * * * *